United States Patent [19]

Andrei et al.

[11] Patent Number: 5,264,307

[45] Date of Patent: Nov. 23, 1993

[54] SOLID, POLYMERIC, POLYETHER BASED ELECTROLYTE

[75] Inventors: Maria Andrei, Berceto; Luca Marchese, Milan; Arnaldo Roggero, San Donato Milanese; Marco Ferrari, Milan, all of Italy

[73] Assignee: Eniriceche S.p.A., Milan, Italy

[21] Appl. No.: 21,199

[22] Filed: Feb. 23, 1993

[30] Foreign Application Priority Data

Apr. 28, 1992 [IT] Italy .................. 1008 A/92

[51] Int. Cl.$^5$ .............................. H01M 6/18
[52] U.S. Cl. .................. 429/192; 429/191; 252/62.2
[58] Field of Search ................ 429/192, 191; 252/62.2

[56] References Cited

U.S. PATENT DOCUMENTS

| | | |
|---|---|---|
| 4,303,748 | 12/1981 | Armand . |
| 4,471,037 | 9/1984 | Bannister . |
| 4,886,716 | 12/1989 | Rogerro et al. . |
| 5,173,205 | 12/1992 | Marchese et al. . |

FOREIGN PATENT DOCUMENTS

| | | |
|---|---|---|
| 13199 | 7/1980 | European Pat. Off. . |
| 13037 | 7/1990 | European Pat. Off. . |
| 2523769 | 9/1983 | France . |
| 2568574 | 7/1984 | France . |

*Primary Examiner*—John S. Maples
*Attorney, Agent, or Firm*—Shea & Gould

[57] ABSTRACT

A solid, polymeric electrolyte is prepared by:
1) blending:
(a) a macromer of formula (I)

$$CH_2=C(CH_3)COO(CH_2CH_2O)_2-\underset{\underset{CH_3}{|}}{CH}-(CH_2CH)_n-OR$$
$$\underset{|}{O}$$
$$(CH_2CH_2O)_x-R$$

wherein R = methyl, ethyl, n is an integer comprised within the range of from 2 to 20, x is an integer comprised within the range of from 2 to 5;
(b) a difunctional comonomer of formula (II)
$CH_2=C(CH_3)COO(CH_2CH_2O)_m-CO-(CH_3)C=CH_2$ wherein m is an integer comprised within the range of from 2 to 5; with a molar ratio of the macromer (I) to the difunctional comonomer (II) comprised within the range of from 98:2 to 60:40;
(c) an ionic compound in an amount comprised within the range of from 1 to 30% by weight;
(d) an oligomer or a dipolar aprotic liquid in an amount comprised within the range of from 0 to 80% by weight;
(e) a photoinitiator in an amount comprised within the range of from 0 to 10% by weight; 2) applying the above mixture on an inert support and exposing it to a source of ultraviolet light, thermal radiations, or electron beam.

15 Claims, 1 Drawing Sheet

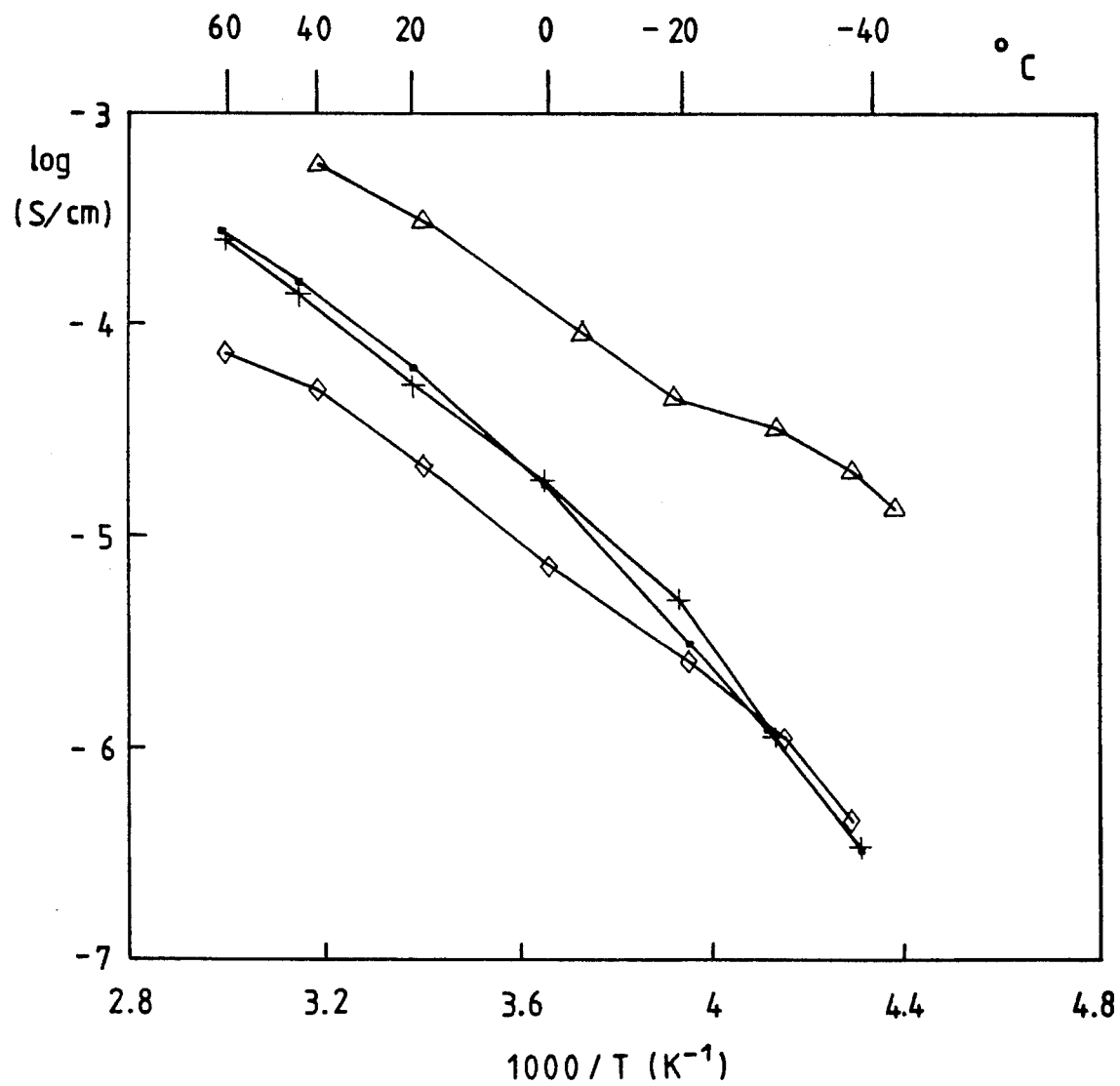

SOLID, POLYMERIC, POLYETHER BASED ELECTROLYTE

The present invention relates to a solid polymeric electrolyte, to the process for preparing it and to its use in the electrochemical devices which contain it.

The solid polymeric electrolytes, also said "ionically conductive polymers" consist of a solid solution of an ionic compound, preferably an alkali metal salt, in a solid polymeric matrix deriving from the polymerization of monomers containing a heteroatom, such as oxygen, nitrogen or sulphur.

The most widely diffused solid polymeric electrolyte are those based on a polyethylene oxide, or on another polyether, such as, for example, those disclosed in U.S. Pat. No. 4,471,037; FR 2,523,769; FR 2,568,574; EP 13,037 and EP 13,199.

Such materials display useful values of ionic conductivity only at higher temperatures than room temperature and furthermore display unsatisfactory mechanical properties which cause a poor dimensional stability of the corresponding membranes.

In U.S. Pat. No. 5,173,205 and IT 1,222,929 particular polymeric polyvinyl ether-based electrolytes are disclosed which display both an improved mechanical strength and a satisfactory conductivity even at relatively low temperatures.

Preparing such materials requires complex multistep processes comprising the copolymerization of suitable vinyl ethers at a temperature of the order of $-75°/-80°$ C. for a time comprised within the range of from 30 to 60 minutes, dissolving the resulting solid, crosslinked polyvinlether in a suitable solvent, blending the polymer with a solution containing an ionic compound and evaporating the solvent in order to obtain a membrane.

In U.S. Pat. No. 5,173,205, crosslinking the suitable functionalized polyvinyl ether is carried out by means of a diprotic crosslinker agent during the step of polymer blending with the ionic compound. This step is followed by solvent evaporation in order to obtain the membrane.

We have found now a solid, polymeric, polyether-based electrolyte which can be directly prepared in the membrane producing step by means of free-radical photopolymerization and which, as compared to the materials disclosed in the prior art, supplies a better performance as regards conductivity and mechanical strength.

Therefore, the subject-matter of the present invention is a solid, polymeric electrolyte, obtainable in membrane form, comprising a solid solution of an ionic compound in a solid, crosslinked polymeric matrix of polyether nature, characterized in that said electrolyte is prepared by:
1) blending:
   (a) a macromer of formula (I)

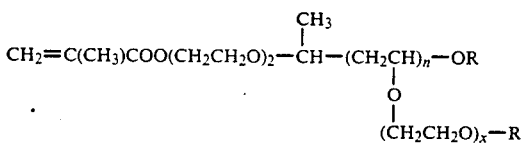

wherein
R = methyl, ethyl, n is an integer comprised within the range of from 2 to 20, x is an integer comprised within the range of from 2 to 5;

(b) a difunctional comonomer of formula (II) $CH_2=C(CH_3)COO(CH_2CH_2O)_m-CO-(CH_3)C=CH_2$ wherein m is an integer comprised within the range of from 2 to 5; with a molar ratio of the macromer (I) to the difunctional comonomer (II) comprised within the range of from 98:2 to 60:40;

(c) an ionic compound in an amount comprised within the range of from 1 to 30% by weight;

(d) an oligomer or a dipolar aprotic liquid in an amount comprised within the range of from 0 to 80% by weight;

(e) a photoinitiator in an amount comprised within the range of from 0 to 10% by weight;

2) applying the above mixture on an inert support and exposing it to a source of ultraviolet light, thermal radiations, or electron beam.

The photoinitiator (e) is present in the reaction mixture only in the case where in the step (2) the radiation source the mixture is exposed to, is a ultraviolet light source. In that case, the photoinitiator (e) is present in an amount comprised within the range of from 0.5 to 10%, preferably of from 1 to 5% by weight. Such a photoinitiator is of the free-radical generator type and, e.g., it may be benzophenone or benzoin methyl ether.

In the step (1), the molar ratio of the macromer (I) to the comonomer (II) is preferably comprised within the range of from 95:5 to 70:30.

The macromer (I) can be prepared by reacting (III) $CH_2=C(CH_3)-COO(CH_2CH_2O)_2-CH=CH_2$ with suitable amounts of vinyl ether (IV) $CH_2=CH-O-(CH_2CH_2O)_x-R$ wherein x and R have the same meaning as reported above for formula (I), in the presence of HI as the polymerization initiator and $I_2$ as a chain extending agent.

The comonomer (II) can be prepared by reacting the corresponding glycol with methacryloyl chloride, in ethyl ether and in the presence of pyridine.

The ionic compound (c) is preferably used in an amount comprised within the range of from 5 to 20% by weight. Such an ionic compound is a salt, preferably a perchlorate, triflate, tetrafluoroborate or hexafluoroarsenate, of (either univalent or multivalent) metals, and, in particular, of lithium, sodium, potassium, calcium, copper, zinc, magnesium, lead, tin and aluminum. Said ionic compound preferably is a lithium salt.

The amount of dipolar aprotic liquid or oligomer is preferably comprised within the range of from 30 to 70% by weight. The dipolar aprotic liquid is selected from solvents endowed with a high dielectric constant, low volatility and dissociating properties for lithium salts and preferably is propylene carbonate, ethylene carbonate, dimethoxy ethane and mixtures thereof.

The oligomer can be selected from polyethylene glycol dialkyl ethers or oligoethylene glycol dialkyl ethers, such as diglyme or tetraglyme.

The blend of step (1) is prepared by blending the components and stirring until a homogeneous solution is obtained.

In the step (2), the support may be a film of an inert plastics material, it may be glass, a metal foil, or it may directly the surface of a lithium anode or of a composite cathode constituted by an oxide or sulfide of a transition metal (V, Mn, Co, Ti, W, Ni) in mixture with an ionic conductive material and an electronic conductor (carbon black or acetylene black).

The polymerization process is rather fast, and it generally lasts a few tens of seconds.

A solid, polymeric electrolyte in membrane form is obtained, with a thickness of the order of 50-200 microns.

The glass transition temperature (Tg) of these polymeric electrolytes is comprised within the range of from $-90°$ C. to $-50°$ C.

The polymeric electrolytes of the present invention display a higher mechanical strength, a higher dimensional stability and a higher conductivity, even at low temperatures, than the polyether based polymeric electrolytes known from the prior art. They can be used with good results as electrolytic separators in electrochemical devices, in optical and electrochromic displays and in sensors. The following experimental results are illustrative, non-limitative of the purview of the present invention.

EXAMPLE 1

Synthesis of
$CH_2=C(CH_3)—COO(CH_2CH_2O)_2—CH=CH_2$ (A)

Diethylene glycol (85 g, 0.8 mol), ethyl vinyl ether (80 ml, 0.8 mol) and, as the catalyst, mercuric acetate $Hg(CH_3COO)_2$ are charged to a 3-neck flask of 250 ml, equipped with condenser and inlets for the reactants and an inert gas. The system is kept under refluxing conditions, at a temperature of 70°-80° C., for 10 hours. The product is recovered by extraction with methylene chloride and is separated from the corresponding divinyl ether by distillation. In that way, 40 g (0.3 mol) of diethylene glycol monovinyl ether is obtained, with a yield of 40%, and is added to a solution containing 40 ml of ethyl ether and 53 ml of pyridine. To the resulting mixture, kept at room temperature and under a flowing nitrogen stream, methacryloyl chloride (38.3 g, 0.37 mol) is added dropwise. The addition of the chloride causes the immediate precipitation of pyridinium hydrochloride. The reaction is discontinued when the disappearance of the monovinyl ether is observed. The product (A) is recovered from the reaction mixture via HPLC, using silica as the stationary phase and a mixture of 8:1 hexane:ethylacetate as the eluent. 42 g of 99%-pure product is obtained, which corresponds to a yield of 70% relatively to diethylene glycol monovinyl ether.

EXAMPLE 2

Synthesis of $CH_2=CH—O—(CH_2CH_2O)_3—CH_3$ (B)

Ethyl vinyl ether (1.8 mol), triethylene glycol monomethyl ether (0.6 mol) and mercuric acetate (0.0057 mol) are charged to a three-neck flask of 500 ml, equipped with reflux condenser, and kept under a flowing nitrogen stream. The reaction mixture is heated at its refluxing temperature for approximately 10 hours. The reaction is then quenched by means of the addition of potassium carbonate and the reaction mixture is distilled, first under atmospheric pressure in order to remove the excess of ethyl vinyl ether and any ethyl alcohol formed as a reaction byproduct, then under reduced pressure, in order to separate the vinyl ether product from the starting glycol. The vinyl ether is obtained with a purity of 99% and a yield, relatively to the starting glycol, of 80%.

EXAMPLE 3

Preparation of

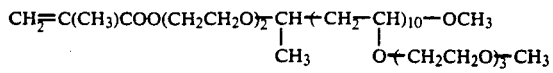

The monomer (A) of Example 1 (300 mg, 1.5 mmol) in 25 ml of anhydrous toluene is charged to a glass reactor of 100 ml of capacity, kept under a flowing nitrogen stream and cooled at $-78°$ C. To the solution, kept vigorously stirred, anhydrous hydrogen iodide HI in n-hexane is added (3.75 ml of a 0.4 M solution, equivalent to 1.5 mmol of HI). The reaction is allowed to proceed for approximately 1 hour. Then, the vinyl ether (B) prepared in example 2 (2.85 g; 15 mmol) and a solution of iodine $I_2$ in toluene (1.6 ml of a 0.47 M solution, equivalent to 0.75 mmol of $I_2$) are added in the sequence stated. The temperature is then increased up to $-40°$ C., and the system is kept with stirring for a further 2 hours. To the reaction mixture methanol saturated with ammonia is added, the reaction mixture is washed with an aqueous solution of sodium thiosulfate in order to eliminate the excess of iodine, is washed with water, the mixture is then extracted with methylene chloride, is dried on sodium sulfate and the macromer is recovered after solvent evaporation.

The molecular weight of the macromer was determined via NMR, was confirmed by GPC, and resulted to be of 2100 g/mol.

EXAMPLE 4

Preparation of

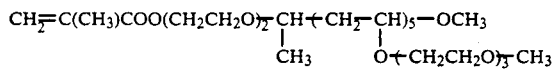

The process is carried out as in Example 3, with a molar ratio of (B):(A)=5. A polymer is obtained which has a molecular weight of 1200 g/mol.

EXAMPLE 5

Preparation of

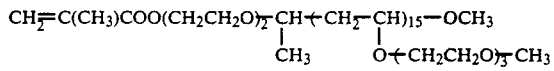

The process is carried out as in Example 3, with a molar ratio of (B):(A)=15. A polymer is obtained which has a molecular weight of 3000 g/mol.

EXAMPLE 6

Preparation of

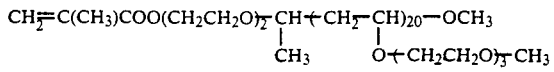

The process is carried out as in Example 3, with a molar ratio of (B):(A)=20. A polymer is obtained which has a molecular weight of 3900 g/mol.

EXAMPLES 7-10

Preparation of electrolytic membranes

Inside a dry-box with an atmospheric humidity level of less than 5 ppm, the macromer prepared according to Example 3, the comonomer of formula $CH_2=C(CH_3)-COO(CH_2CH_2O)-CO-(CH_3)C=CH_2$, with a molar ratio of macromer:comonomer of 75:25, $LiCF_3SO_3$ as the ionic compound, propylene carbonate as the dipolar aprotic liquid and benzophenone as the photoinitiator are mixed in the amounts as shown in the following Table, as percent by weight values.

|  | Preparation | | | |
| --- | --- | --- | --- | --- |
|  | 1 | 2 | 3 | 4 |
| Macromer | 42.6 | 39.7 | 44 | 29.9 |
| Comonomer | 2 | 1.8 | 2 | 1.3 |
| $LiCF_3SO_3$ | 10 | 16.2 | 7.2 | 7 |
| Propylenecarbonate | 42.6 | 39.7 | 44 | 59.8 |
| Photoinitiator | 2.8 | 2.6 | 2.8 | 2 |

The resulting blends are cast as a constant-thickness film on a glass support and are submitted to U.V. radiation for a time period of 120 seconds. In that way, 4 homogeneous electrolytic membranes where obtained which displayed good dimensional stability, a thickness of approximately 100 microns and a glass transition temperature (Tg) as indicated in the following Table:

|  | 1st Prep. | 2nd Prep. | 3rd Prep. | 4th Prep. |
| --- | --- | --- | --- | --- |
| Tg (°C.) | −61 | −56 | −80 | −89 |

In the Figure, the charts are reported of the ionic conductivity as measured by impedance spectroscopy at the temperatures of 60° C., 40° C., 20° C., 0° C., −10° C., −20° C., and −40° C., within the frequency range of from 0.5 Hz to 65000 Hz. The measurements were carried out by applying and alternated sinusoidal potential difference, of magnitude of 100 mV, between two carbon steel electrodes, between which the polymeric membrane is compressed.

In the Figure, in particular:

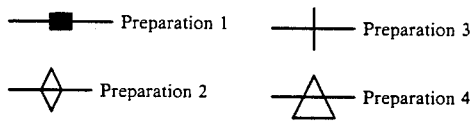

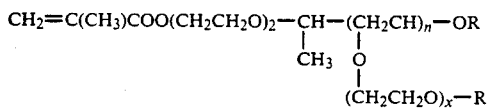

We claim:

1. Solid, polymeric electrolyte, comprising a solid solution of an ionic compound in a solid, crosslinked polymeric matrix of polyether, characterized in that said polymeric electrolyte is prepared by:
 1) preparing a mixture containing:
    (a) a macromer of formula (I)

$$CH_2=C(CH_3)COO(CH_2CH_2O)_2-\underset{\underset{(CH_2CH_2O)_x-R}{\overset{|}{O}}}{\overset{|}{CH}}-(CH_2CH)_n-OR$$
$$\phantom{CH_2=C(CH_3)COO(CH_2CH_2O)_2-}\underset{}{\overset{|}{CH_3}}$$

wherein
R is methyl or ethyl,
n is an integer within the range of from 2 to 20,
x is an integer within the range of from 2 to 5;
    (b) a difunctional comonomer of formula (II)
    $CH_2=C(CH_3)COO(CH_2CH_2O)-_m-CO-(CH_3)C=CH_2$ wherein m is an integer within the range of from 2 to 5; with a molar ratio of the macromer (I) to the difunctional comonomer (II) within the range of from 98:2 to 60:40;
    (c) an ionic compound in an amount within the range of from 1 to 30% by weight;
    (d) an oligomer or a dipolar aprotic liquid in an amount within the range of from 0 to 80% by weight;
    (e) a photoinitiator in an amount within the range of from 0 to 10% by weight;
 (2) applying the above mixture on an inert support and exposing it to a source of ultraviolet light, thermal radiation, or electron beam, with the amount of the component (e) present in the mixture being larger than zero only in the case of exposure to ultraviolet light.

2. Polymeric electrolyte according to claim 1, in which the molar ratio of macromer (I) to comonomer (II) is within the range of from 95:5 to 70:30.

3. Solid, polymeric electrolyte according to claim 1, in which the ionic compound is present in an amount within the range of from 5 to 20% by weight.

4. Solid, polymeric electrolyte according to claim 1, in which the ionic compound is a salt of a metal selected from the group consisting of lithium, sodium, potassium, calcium, copper, zinc, magnesium, lead, tin and aluminum.

5. Solid, polymeric electrolyte according to claim 4, in which the salt is selected from the group consisting of perchlorate, triflate, tetrafluoroborate, and hexafluoroarsenate.

6. Solid, polymeric electrolyte according to claim 4, in which said metal is lithium.

7. Solid, polymeric electrolyte according to claim 1, in which the dipolar aprotic liquid is present in an amount within the range of from 30 to 70% by weight.

8. Solid, polymeric electrolyte according to claim 1, in which the dipolar aprotic liquid is propylene carbonate, ethylene carbonate, dimethoxyethane or mixtures thereof.

9. Electrolyte according to claim 1, in which the oligomer is selected from oligoethylene glycol dialkyl ethers, and polyethylene glycol dialkyl ethers.

10. Electrolyte according to claim 1, in which the photoinitiator is in an amount within the range of from 0.5 to 10% by weight.

11. Electrolyte according to claim 1, in which the photoinitiator is benzophenone or benzoin methylether.

12. Electrolyte according to claim 1, in which the support is a film of an inert plastics material, glass, metal foil, or a surface of a composite cathode constituted by an oxide or sulfide of a transition metal in mixture with an ionically conductive material and an electronic conductor.

13. Electrolyte according to claim 9, wherein the oligoethylene glycol dialkyl ether is diglyme or tetraglyme.

14. Electrolyte according to claim 10, wherein the photoinitiator is within the range of from 1 to 5%.

15. Electrolyte according to claim 1, in membrane form, used as an electrolytic separator in electrochemical devices, optical and electrochromic displays and sensors.

* * * * *